(12) United States Patent
Breuer et al.

(10) Patent No.: US 8,890,713 B2
(45) Date of Patent: Nov. 18, 2014

(54) DEVICE AND METHOD FOR OUTPUTTING A SIGNAL WHEN THERE IS A HAZARDOUS UNDERLYING SURFACE UNDER A VEHICLE

(75) Inventors: Karsten Breuer, Lauenau (DE); Bijan Gerami-Manesch, Burgdorf (DE); Daniel Hanslik, Isernhagen (DE); Guido Hoffmann, Burgwedel (DE); Dirk Sandkuhler, Seelze (DE)

(73) Assignee: WABCO GmbH, Hannover (DE)

( * ) Notice: Subject to any disclaimer, the term of this patent is extended or adjusted under 35 U.S.C. 154(b) by 67 days.

(21) Appl. No.: 13/704,798

(22) PCT Filed: Apr. 29, 2011

(86) PCT No.: PCT/EP2011/002142
§ 371 (c)(1),
(2), (4) Date: Dec. 17, 2012

(87) PCT Pub. No.: WO2012/000579
PCT Pub. Date: Jan. 5, 2012

(65) Prior Publication Data
US 2014/0049405 A1    Feb. 20, 2014

(30) Foreign Application Priority Data
Jun. 30, 2010  (DE) .......................... 10 2010 025 719

(51) Int. Cl.
| | | |
|---|---|---|
| *G08G 1/09* | (2006.01) | |
| *G08G 1/0967* | (2006.01) | |
| *B60Q 9/00* | (2006.01) | |
| *B60T 8/172* | (2006.01) | |
| *G01B 11/30* | (2006.01) | |
| *G01N 21/21* | (2006.01) | |
| *G01N 21/35* | (2014.01) | |
| *G01N 21/31* | (2006.01) | |
| *G01N 21/55* | (2014.01) | |

(52) U.S. Cl.
CPC ............ *G08G 1/096766* (2013.01); *B60Q 9/00* (2013.01); *B60Q 9/002* (2013.01); *B60T 8/172* (2013.01); *G01B 11/303* (2013.01); *G01N 21/21* (2013.01); *G01N 21/35* (2013.01); *B60Q 2400/50* (2013.01); *B60T 2210/12* (2013.01); *G01N 21/314* (2013.01); *G01N 21/3563* (2013.01); *G01N 21/55* (2013.01); *G01N 2021/3185* (2013.01); *G01N 2201/0216* (2013.01); *G01N 21/3554* (2013.01)
USPC .......................................... 340/905; 340/901

(58) Field of Classification Search
USPC .................................................. 340/901, 905
See application file for complete search history.

(56) References Cited

U.S. PATENT DOCUMENTS

| 4,274,091 A | 6/1981 | Decker |
| 4,668,859 A | 5/1987 | Winterer |

(Continued)

FOREIGN PATENT DOCUMENTS

| DE | 2 256 885 | 5/1974 |
| DE | 197 22 829 | 12/1998 |

(Continued)

*Primary Examiner* — Eric M Blount
(74) *Attorney, Agent, or Firm* — Kramer Levin Naftalis & Frankel LLP

(57) ABSTRACT

A method and a device for outputting a signal when there is a hazardous surface under a vehicle includes providing an optical surface sensor for determining one or more parameters of the underlying surface, a stationary-state-determining device for determining whether the vehicle is stationary or is to be brought to a standstill, and an output device that outputs a signal if the underlying surface has been determined to be hazardous on the basis of the parameter(s), and the vehicle is stationary or is to be brought to a standstill.

23 Claims, 4 Drawing Sheets

(56) References Cited

U.S. PATENT DOCUMENTS

| | | | |
|---|---|---|---|
| 5,467,071 A * | 11/1995 | Koenig | 340/433 |
| 5,521,594 A * | 5/1996 | Fukushima | 340/901 |
| 5,652,655 A | 7/1997 | Uno et al. | |
| 5,818,339 A * | 10/1998 | Giles et al. | 340/583 |
| 6,023,220 A | 2/2000 | Dobler et al. | |
| 6,505,714 B1 | 1/2003 | Ward | |
| 6,948,595 B2 | 9/2005 | Audren et al. | |
| 7,107,138 B2 * | 9/2006 | Currie | 701/79 |
| 7,192,172 B1 * | 3/2007 | Alberti | 362/543 |
| 7,301,478 B1 * | 11/2007 | Chinn et al. | 340/905 |
| 7,374,026 B2 | 5/2008 | Taylor et al. | |
| 7,548,805 B2 | 6/2009 | Yamaguchi et al. | |
| 7,614,483 B2 | 11/2009 | Klinger et al. | |
| 7,615,750 B2 * | 11/2009 | Dupont et al. | 250/339.11 |
| 8,044,823 B2 * | 10/2011 | Doherty et al. | 340/905 |
| 2002/0075141 A1 | 6/2002 | Lang et al. | |
| 2005/0259033 A1 | 11/2005 | Levine | |
| 2006/0220801 A1 * | 10/2006 | Bauer et al. | 340/425.5 |
| 2006/0261975 A1 | 11/2006 | Fridthjof | |
| 2008/0133098 A1 | 6/2008 | Wang et al. | |
| 2008/0217117 A1 | 9/2008 | Severinsson et al. | |
| 2008/0283345 A1 | 11/2008 | Balz et al. | |
| 2011/0017554 A1 * | 1/2011 | Baehrle-Miller et al. | 188/72.1 |
| 2012/0065858 A1 * | 3/2012 | Nickolaou et al. | 701/70 |

FOREIGN PATENT DOCUMENTS

| | | |
|---|---|---|
| DE | 10 2005 005 250 A1 | 9/2005 |
| DE | 10 2005 022 404 A1 | 11/2006 |
| DE | 699 31 453 T2 | 12/2006 |
| DE | 10 2005 027 915 A1 | 1/2007 |
| DE | 60 2004 009 422 | 11/2007 |
| DE | 60 2005 003 162 T2 | 12/2007 |
| DE | 10 2008 009 161 A1 | 9/2008 |
| DE | 10 2007 022 510 | 11/2008 |
| DE | 10 2007 043 968 A1 | 1/2009 |
| DE | 10 2008 038 037 | 2/2010 |
| EP | 1 215 638 | 6/2002 |
| EP | 1 384 913 A2 | 1/2004 |
| JP | 2001 099 779 | 4/2001 |
| WO | WO 02/081250 | 10/2002 |
| WO | WO 2007/051809 A1 | 5/2007 |
| WO | WO 2010/019045 | 2/2010 |

* cited by examiner

DEVICE AND METHOD FOR OUTPUTTING A SIGNAL WHEN THERE IS A HAZARDOUS UNDERLYING SURFACE UNDER A VEHICLE

FIELD OF THE INVENTION

The present invention generally relates to sensors for outputting a warning signal as a function of the roadway condition under a vehicle.

BACKGROUND OF THE INVENTION

To warn of slippery roads or other hazardous roadway states, modern motor vehicles typically have external temperature sensors having a corresponding display as standard equipment, in order to give the driver or vehicle occupants a warning, for example, if the external temperature sinks below +3° C., for example. Therefore, the driver is to be warned before the occurrence of possible slippery ice or winter road conditions as a precaution. Such warning messages are of a general nature, however, and are independent of the actual roadway state, so that they are only perceived by the driver and/or a vehicle occupant as marginal information, if at all. In practice, such temperature messages are frequently ignored.

In order to obtain information about the roadway surface actually located under the motor vehicle, light-based optical surface sensors or mechanical or acoustic sensors are known. However, these share the feature of only being able to provide satisfactory results when the vehicle moves in relation to the surface.

A method and a device for outputting a warning signal for the vehicle driver, in order to warn about a slippery underlying surface, is known from WO 2002/081250 A1. The triggering of the warning is based on slip values ascertained on a rotating wheel. This system can only be used when the vehicle is moving.

However, many accidents or hazardous situations result when the vehicle is stopped and occupants get out, or the vehicle and optionally trailers, respectively, are to be parked.

SUMMARY OF THE INVENTION

Generally speaking, it is an object of the present invention to provide a improved slipperiness warning device and method. A device according to an embodiment of the present invention comprises an optical surface sensor for determining at least one parameter of the underlying surface under the vehicle, a stoppage ascertainment unit for ascertaining whether the vehicle is stationary or is to be brought to a stop, and an output unit, which outputs a signal when the underlying surface has been ascertained to be hazardous on the basis of the at least one parameter and the vehicle is stationary or is to be brought to a stop.

A method according to an embodiment of the present invention comprises emitting light of at least one wavelength onto the underlying surface, detecting light of the at least one wavelength reflected on the underlying surface, and ascertaining on the basis of the detected reflected light whether the underlying surface is hazardous. Simultaneously or offset in time before or after thereto, the method comprises ascertaining whether the vehicle is stationary or is to be brought to a stop and outputting a signal if the underlying surface has been ascertained to be hazardous and it has been ascertained that the vehicle is stationary or is to be brought to a stop.

Using such a device or using the method, respectively, vehicle occupants, both the driver and also passengers or navigators, can be warned before exiting by the signal, for example, a warning signal or a warning tone, that a slippery or otherwise hazardous underlying surface is located under the vehicle. In this case, the signal output by the output unit is a warning signal. The output unit can comprise a display unit for outputting the warning signal and can be arranged, for example, in the vehicle door or in proximity to the vehicle door, in order to warn an occupant of the vehicle before exiting the vehicle when there is a hazardous underlying surface. Such a display can be provided both in passenger automobiles and also in public transportation vehicles, such as, for example, omnibuses, streetcars, or trains.

The signal of the output unit can also be a control signal, which is output to a central display unit, a central vehicle controller, and/or to further elements. The further elements can be a door lock, a trailer coupling unit, or other elements.

The surface sensor can be arranged on or under or in the region of a vehicle door in order to detect the actual condition of the roadway surface or the underlying surface in the region of the corresponding vehicle doors.

The condition of the roadway or the underlying surface can comprise a state of the roadway surface, such as wet, dry, icy, or snow-covered or a combination thereof. The condition can additionally or alternatively also comprise the type of the roadway or information about a roughness of the roadway or roadway surface, such as asphalt, concrete, split, or gravel or a combination thereof. The hazardous underlying surface can be a slippery underlying surface such as an underlying surface covered with slippery ice or snow or a corresponding roadway surface. However, the hazardous underlying surface can also be a water surface or a puddle or a soft underlying surface such as sand or grass.

The optical surface sensor can comprise a light source unit for emitting light of at least one wavelength onto the underlying surface and at least one detector for detecting light reflected from the underlying surface.

The surface sensor can comprise, in addition to the first detector, a second detector, wherein the first detector is capable of detecting diffusely reflected light and the second detector is capable of detecting specularly reflected light. At least two polarizers can be provided, wherein a first polarizer having a first polarization unit is assigned to the first detector. The light source unit can be a light source polarizer and/or a second polarizer can be assigned to the second detector, whose polarization direction(s) is/are aligned substantially perpendicularly to the first polarization direction of the first polarizer. If at least two polarizers or polarization filters are provided, the first polarizer is arranged on the first detector, which only transmits light waves in the first polarization direction to the first detector. If a light source polarizer is provided on the light source unit, its polarization direction is arranged substantially perpendicularly to the first polarization direction of the first polarizer, and the light emitted by the sensor is polarized in a direction substantially perpendicular to the first polarization direction, so that specularly reflected light that is polarized on the first detector is filtered out and only diffusely reflected light is detected. A similar effect can be achieved if a second polarizer is arranged in front of the second detector, whose polarization direction is aligned substantially perpendicularly to the first polarization direction. The second polarizer can be used alternatively or additionally to the light source polarizer, it can also be provided that already polarized light is generated in the light source unit.

The light source unit can be designed to emit light of at least two different wavelengths or to emit multiple wavelengths onto the underlying surface or the roadway surface. For this purpose, the light source unit can comprise multiple light sources, for example. The use of at least two, preferably three different wavelengths allows the sensor to be operated in a spectral manner. Through the use of wavelengths that are absorbed particularly well by ice or water, for example, ice or water can be recognized on the roadway or roadway surface when the reflected light of the wavelength absorbed by water or ice is compared to that of a reference wavelength. It is therefore possible to execute the principles of spectral analysis and diffuse and specular reflection in only one apparatus, or in a single housing. The light source unit, the first detector, and optionally the second detector can be arranged for this purpose in a shared single and/or one-piece housing, for example, directly adjacent to one another.

Light in at least three different wavelengths in the infrared range can be used. The light source unit can comprise multiple light sources for this purpose. For example, the light source unit can be configured to emit infrared light of the wavelengths 1300 nm, 1460 nm, and 1550 nm. While light of the wavelength 1460 nm is absorbed particularly well by water, light of the wavelength 1550 nm is absorbed well by ice. Light in the range of approximately 1300 nm can then be used as a reference wavelength. However, other wavelengths can also be used. In particular for the reference wavelength, any other wavelength can be used that is not noticeably absorbed by either ice or water. Any other wavelength that is absorbed to an increased extent in water can also be used as a water-sensitive wavelength. Any wavelength that is absorbed to an increased extent in ice can similarly be selected as an ice-sensitive wavelength. Other wavelengths of interest comprise, e.g., 1190, 1040, 970, 880, and 810 nm in the infrared range, as well as the visible wavelengths 625, 530, and 470 nm.

The light source unit can be designed to emit light of precisely three different wavelengths. For this purpose, the light source unit can have three light sources, one light source for each wavelength. Only the three wavelengths are used to detect both spectral light and also specularly/diffusely reflected light, in order to ascertain or recognize both the roadway condition and also the type of the roadway. Each of the light sources can be individually activatable and can be turned on and off and/or regulated in intensity independently of the others.

In addition, more than the above-mentioned two or three different wavelengths can also be used. For example, the wavelength 625 nm can also be used for measuring the diffusely and specularly reflected light.

Furthermore, the emitted light can be modulated in intensity or amplitude by turning on and off all or individual light sources of the light source unit. The modulation of the intensity or the turning on and off can be performed separately for each wavelength of the light source unit or for each light source of the light source unit. For example, the modulation of the amplitude or intensity or the turning on and off, respectively, can be performed for each wavelength at the same frequency, but phase-shifted, and/or at different frequencies. Thus, for example, the light of different wavelengths can be emitted offset in time or sequentially. For example, light of a first wavelength can be emitted for a specific time interval, then the light of the first wavelength can be turned off and a second wavelength turned on, etc. Light of only one wavelength at a time is then detected in the detectors. A spectral analysis or splitting of the incident light on the detectors can thus be avoided. Mixed forms of various modulation techniques are also applicable, in particular frequency-modulated and amplitude-modulated optical signal trains with or without interruptions.

The present invention therefore also allows simple detectors to be used as the first or second detector. For example, photodiodes can be used. The first detector and the second detector can each comprise one or more photodiodes. At least the first detector can be designed for the purpose of detecting light of all wavelengths emitted by the light source unit. The detector can alternatively or additionally also comprise an optoelectronic chip (e.g., CCD) or another optical recording unit.

The first detector and the second detector can be used for detecting or ascertaining specularly reflected light and diffusely reflected light. In addition, at least one of the first detector and the second detector can also be used for the spectral ascertainment. At least this detector is then designed for the purpose of detecting light of multiple wavelengths. In this example, the sensor has precisely the first detector and the second detector and no further detectors are provided.

The surface sensor can also comprise an analysis unit, which outputs information about the condition of the roadway surface or the underlying surface.

The above-mentioned stoppage ascertainment unit for ascertaining whether the vehicle is stationary or is to be brought to a stop is used for the purpose of only outputting the signal when it is also relevant. The stoppage ascertainment unit can be connected to the optical surface sensor, in particular to the analysis unit, and can use data of the optical surface sensor for stoppage ascertainment. For example, the stoppage ascertainment unit can detect the light intensity over a predetermined time interval. If the underlying surface under the vehicle does not change, i.e., the vehicle is stationary, the detected light intensity only changes within the system-related error, i.e., within a predetermined variance. If the vehicle moves in relation to the underlying surface, the change or variance of the reflected light becomes greater and exceeds the predetermined value, so that a vehicle movement can be concluded from the detected intensity of the reflected light. The surface sensor can therefore be used as a data generator for the stoppage ascertainment unit or the stoppage ascertainment unit can be integrated in the surface sensor.

However, other stoppage recognition units can be used with the present invention, for example, velocity sensors, which are used on the wheels, for example.

For example, the stoppage ascertainment unit can also be combined with a transit stop brake of a public transit vehicle, in particular an omnibus.

The surface sensor can be arranged in proximity to a vehicle door and detect the underlying surface under the vehicle door, so that a warning message can be output to a vehicle occupant if the underlying surface in front of the vehicle door is slippery, wet, and/or otherwise hazardous. The display can be performed as an optical warning signal on the vehicle door or in proximity to the vehicle door, no matter whether the vehicle is a passenger automobile, an omnibus or another vehicle for public transit, or another utility vehicle. The output unit can also comprise a projector, in order to project a warning signal onto the underlying surface in front of the vehicle door, for example, and thus warn the exiting occupants or passengers accordingly.

A warning signal can also be attached in proximity to or on a vehicle door, in particular on the door opener, for example, and can output a warning signal or an optical display if the underlying surface is hazardous and/or the door opener is actuated. Disengaging a safety belt also comes into consideration in this regard in passenger automobiles as a stoppage ascertainment.

The output unit can also be arranged in proximity to a coupling unit for a vehicle trailer and a warning signal can be output in order to warn the vehicle driver against decoupling or coupling a trailer on a slippery underlying surface.

Still other objects and advantages of the present invention will in part be obvious and in part be apparent from the specification.

The present invention accordingly comprises the features of construction, combination of elements, arrangement of parts, and the various steps and the relation of one or more of such steps with respect each of the others, all as exemplified in the constructions herein set forth, and the scope of the invention will be indicated in the claims.

BRIEF DESCRIPTION OF THE DRAWINGS

Further details and examples of the invention are specified hereafter, solely as examples and in a nonrestrictive manner, with reference to the appended figures, in which.

DETAILED DESCRIPTION OF THE PREFERRED EMBODIMENTS

Figure 1:
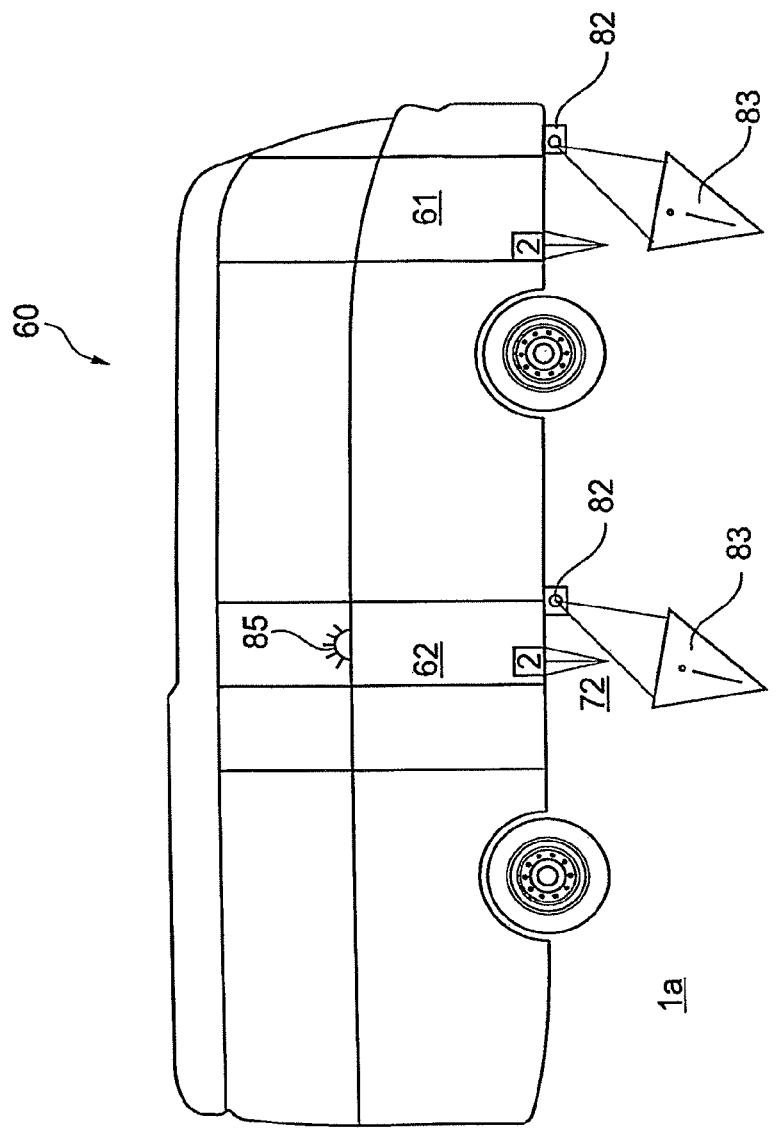
FIG. 1 shows a vehicle including a device according to an embodiment of the present invention.

FIG. 1 shows an example of how a device 9 for outputting a signal when there is a hazardous underlying surface under a vehicle 60 for passenger transport can be arranged. The vehicle 60 can be an omnibus or another vehicle for passenger transport. The vehicle 60 can fundamentally be any other vehicle, for example, rail-bound vehicles, passenger automobiles, or other utility vehicles. The omnibus 60 shown as an example has a front door 61 and a door 62, as is typical in many omnibuses 60 for public transport or long-range travel. The number of doors and the use of double or single doors can vary depending on the vehicle 60, and further doors can be provided, for example, in the rear region of the vehicle.

A device 9 according to the invention is attached in each case in the region of the front door 61 and in the region of the rear door 62 in the example shown. Instead of the complete device 9 according to the invention, only specific elements and units of the device 9, for example, a surface sensor 2, can be arranged in the region of the front or rear doors 61, 62, respectively. In addition to the surface sensor 2, a projector 82 of an output unit 8 can also be arranged in the region of the vehicle doors 61, 62. The projector 82 can be designed for the purpose of projecting a warning signal 83 in the region in front of the vehicle doors 61, 62 onto the roadway surface 1a.

The projected warning signal 83 is only displayed by the output unit 8 when the vehicle 60 is stationary or is to be brought to a stop and when the surface sensor 2 has recognized a hazardous underlying surface 1, for example, an icy roadway 72, as shown in FIG. 1, a water layer 71, a snow-covered roadway, or another underlying surface that is hazardous for exiting or entering passengers. In the case of a water layer 71 on the underlying surface, the surface sensor 2 can also output the warning signal as a function of an ascertained water depth d1 and thus warn of puddles or other water accumulations. The warning signal 83 can comprise different warning symbols for a wet, icy, and/or snowy underlying surface and/or further symbols or characters.

Alternatively or additionally, the vehicle 60 can also have a warning display 85, which is shown in the rear door 62 in FIG. 1, for example. The warning display 85 can have a warning signal and/or a warning color and can notify passengers of a hazardous underlying surface 1 before they exit. The warning display 85 can comprise different warning symbols for a wet, icy, and/or snowy surface 1a of the underlying surface 1 and/or further symbols or characters. The warning display 85 can also be attached at other points in the vehicle 60, for example, in proximity to a coupling device for a trailer or on the trailer itself, to warn against a decoupling and/or coupling procedure on a hazardous underlying surface.

Figure 2:
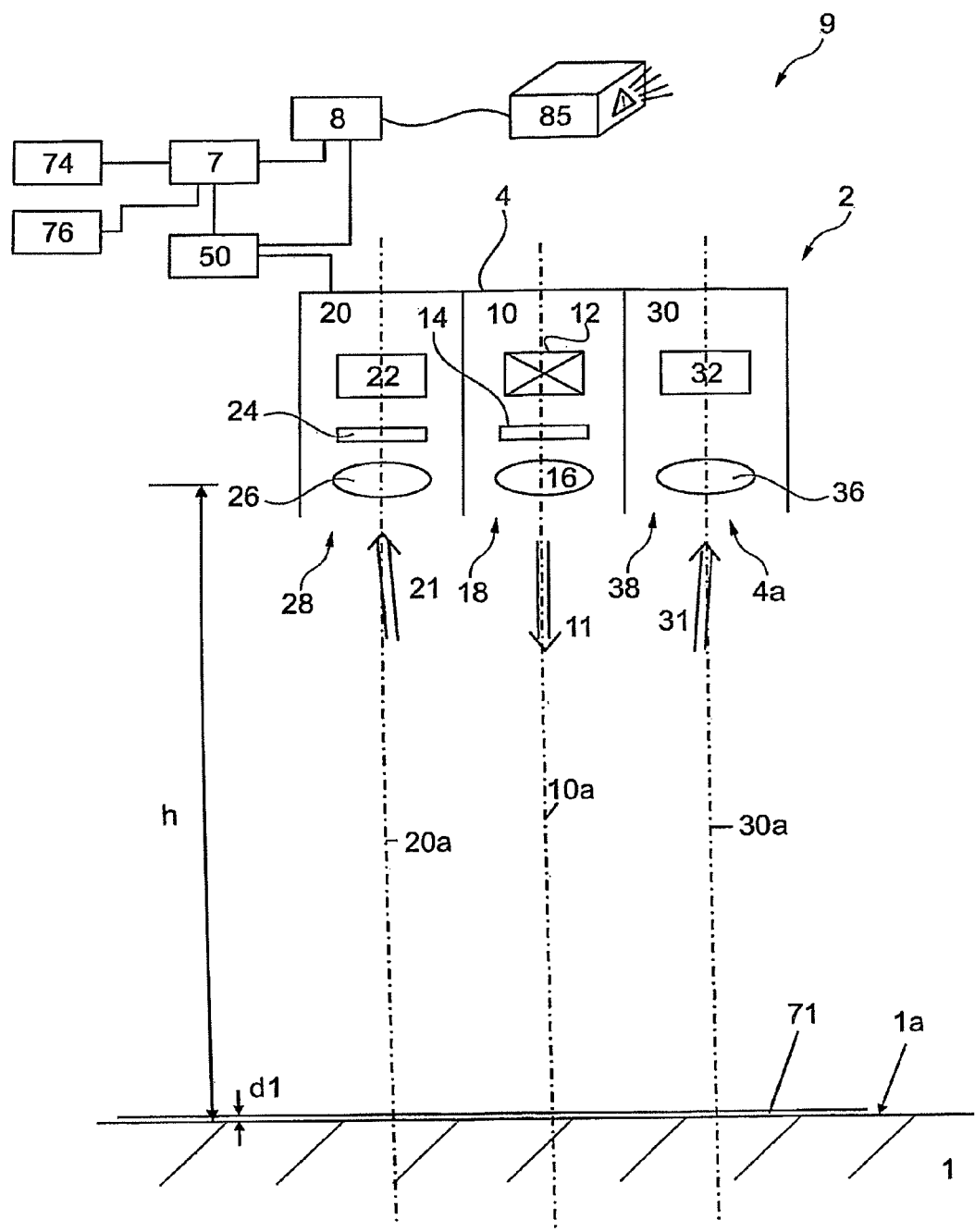
FIG. 2 shows a first exemplary embodiment of a device according to the present invention.

FIG. 2 shows the device 9. The device 9 has a surface sensor 2, a stoppage ascertainment unit 7, and an output unit 8. The surface sensor 2 comprises a light emitter unit 10 and at least one first detector unit 20. A second detector unit 30 is also provided in the example shown. The surface sensor 2 can be a commercially-available surface sensor 2 designed for the optical detection of the roadway condition of the roadway surface 1a.

The surface sensor 2, also designated herein as the sensor 2 for recognizing the condition, in particular a state and the type of the surface of a roadway 1 or roadway surface 1a, respectively, is designed for the purpose of being attached to a motor vehicle 60. In the illustrated example, a water film 71 of the thickness d1 is located on the roadway surface 1a. The roadway surface can also be snow-covered, icy, or dry or can have another condition.

The sensor 2 comprises three units in a housing 4, a light emitter unit 10, a first detector unit 20, and a second detector unit 30. The light emitter unit 10 has a light emitter window or a light emitter opening 18 in the housing 4, the first detector unit 20 has a first detector window or a first detector opening 28 in the housing 4, and the second detector unit 30 has a second detector window or a second detector opening 38 in the housing 4. The light emitter opening 18, the first detector opening 28, and the second detector opening 38 are arranged on the same side 4a of the housing 4 and are aligned toward the roadway 1 when the sensor 2 is installed in an operationally-ready manner on a vehicle. The sensor 2 is aligned so that the emitted light beam 11 is incident approximately perpendicularly on the roadway 1 or the roadway surface 1a, i.e., the optical axis of the light emitter section 10a or the light emitter axis 11a is substantially perpendicular to the roadway 1 or the roadway surface 1a. In the illustrated example, a water film 71 of the thickness d1 is located on the roadway surface 1a. However, the roadway surface can also be snow-covered, dry, or icy or can have another condition.

Figure 3:
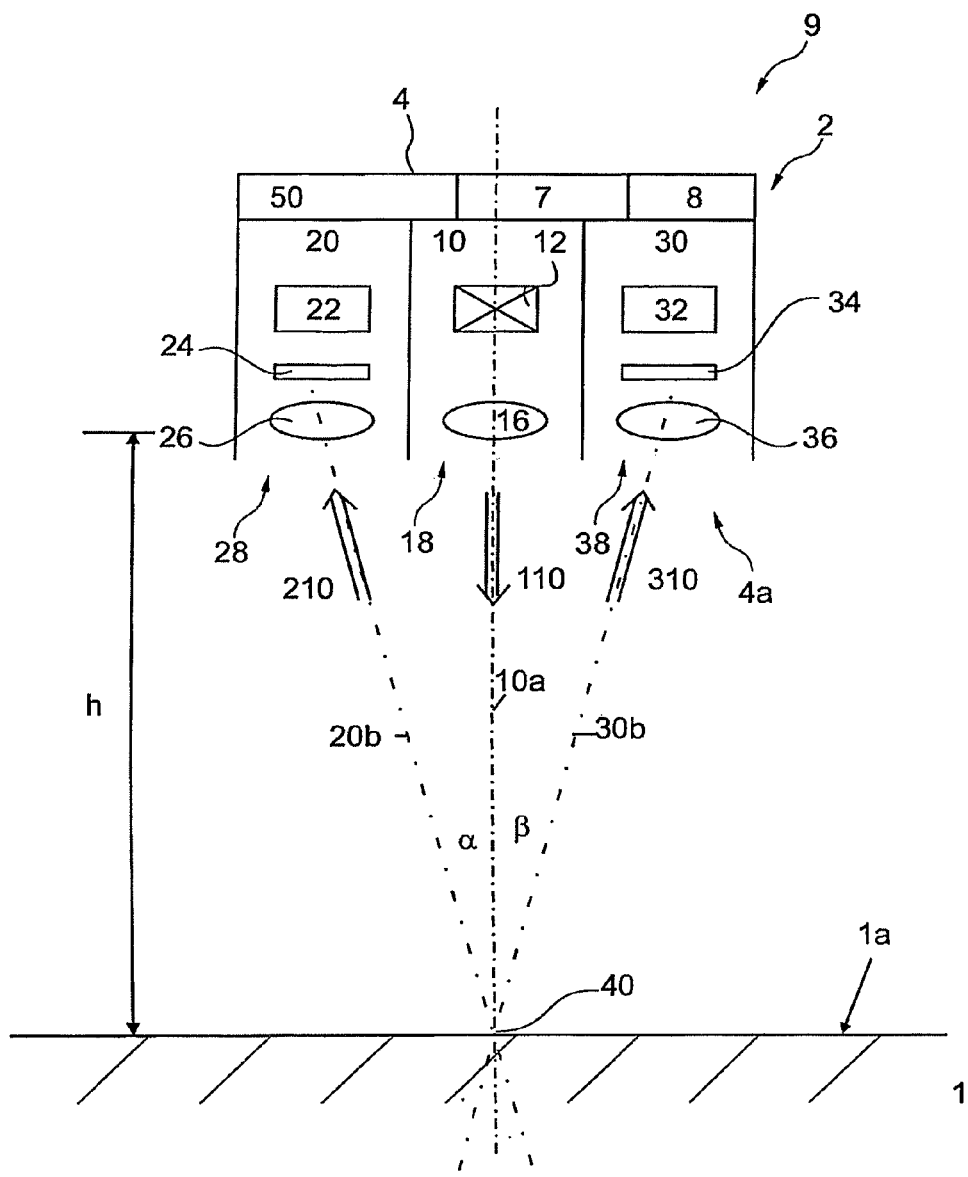
FIG. 3 shows a second exemplary embodiment of a device according to the present invention.

In the examples shown in FIGS. 2 and 3, the light emitter unit 10, the first detector unit 20, and the second detector unit 30 are arranged in a row and the light emitter unit 10 is arranged between the first detector unit 20 and the second detector unit 30.

The light emitter unit 10, the first detector unit 20, and the second detector unit 30 can also be arranged separately from one another, however, and do not have to be combined in one housing.

A light source unit 12, which is designed for emitting light of multiple different wavelengths, is arranged in the light emitter unit 10. The light source unit 12 can comprise one or more light-emitting diodes (LEDs), laser diodes, another suitable light source, or a combination thereof for this purpose and is capable of emitting light of multiple different wavelengths for this purpose. For example, the light source unit 12 can emit light at least having the wavelengths 1300 nm, 1460 nm, and 1550 nm. The provided wavelengths can be adapted to the respective intended use.

In the example shown in FIG. 2, a light source polarizer or light source polarization filter 14, which polarizes the light emitted by the light source unit 12 in a predetermined direction, is connected downstream from the light source unit 12 in the direction of the emitted light beam 11.

Furthermore, an emitter optic 16 is provided, in order to align or focus the emitted light along an emitted light beam 11 on a specific region on the underlying surface or the roadway 1 or the roadway surface 1a under the vehicle 60. The optical axis of the emitter optic 16 can define the optical axis 10a of the light emitter section 10. The emitter optic 16 can consist of one emitter lens or can comprise multiple lenses and/or another optical element.

The first detector section 20 comprises a first detector 22, for example, one or more photodiodes, designed for the purpose of detecting light of all wavelengths emitted by the light source unit 10. The first detector 22 can also comprise multiple photodiodes arranged adjacent to one another or one or more optoelectronic units (e.g., CCD, CMOS) for this purpose.

A first converging optic 26 and a first polarizer or first polarization filter 24 are arranged on the first detector 22. The first converging optic 26 can consist of a single first converging lens or can comprise multiple lenses and/or further optical elements. The polarization direction of the first polarization filter 24 is perpendicular to that of the light source polarization filter 14 and is therefore substantially perpendicular to the predetermined polarization direction. Specularly reflected light, which is polarized in the predetermined direction, is therefore filtered out and only diffusely reflected light reaches the first detector 22. The first detector 22 is therefore used as a "scatter detector".

A first axis 20a can substantially correspond to the optical axis of the first converging optic 26 and/or the first detector section 20 and can be aligned substantially parallel to the emitter axis 10a, which substantially corresponds to the optical axis of the emitter optic 16 and/or the light emitter section 10.

A second detector 32 is arranged in the second detector section 30, which is arranged on the side of the light emitter section 10 opposite to the first detector section 20 in the housing 4 of the sensor 2.

The second detector 32 can also comprise a photodiode, which is designed for the purpose of at least detecting light of one of the wavelengths emitted by the light source unit 12. The second detector 32 can also comprise multiple photodiodes arranged adjacent to one another, and can be designed for the purpose of detecting light of multiple different wavelengths or wavelength ranges.

A second converging optic 36 is assigned to the second detector 32, in order to focus the reflected light on the second detector 32 and detect it therein. The second converging optic 36 can consist of a single second converging lens or can comprise multiple lenses and/or further optical elements. In contrast to the first detector 22, the second detector 32 in the example shown in FIG. 1 does not have a polarizer or polarization filter. Since the emitted light is already polarized, this is also not necessary. Therefore, diffusely reflected light and specularly reflected light, which is reflected along the second detector beam path 31, is detected by the second detector. However, the second detector 32 can also have a polarization filter (not shown), whose polarization direction is parallel to that of the emitter polarizer 16, in order to only detect specularly reflected light in the second photodiode 36.

A second axis 30a can substantially correspond to the optical axis of the second converging optic 36 and/or the second detector section 30 and can be aligned substantially parallel to the emitter axis 10a, which substantially corresponds to the optical axis of the emitter optic 16 and/or the light emitter section 10.

The described sensor can be operated in the visible light range, for example, at a wavelength of approximately 625 nm, in order to measure specularly reflected light and diffusely reflected light. The roadway brightness and roadway roughness can be concluded from the ratio of the diffusely reflected light measured in the first detector the specularly reflected light additionally measured in the second detector 32, and it can therefore be determined whether the vehicle is located on an asphalt or concrete roadway, for example.

The described sensor can also be used in the infrared range at various wavelengths. The first detector 22 and/or the second detector 32 can be used for this purpose. For example, infrared light of the wavelength 1460 nm is absorbed particularly well by water, so that light of this wavelength is only reflected back to the first detector 22 or the second detector 32 to a small extent in the event of a wet roadway. In the event of a dry roadway, this wavelength is reflected normally, in contrast infrared light of the wavelength 1550 nm is absorbed well by ice. Through comparison of the reflection of these two wavelengths and consideration of a reference wavelength, the presence of ice or water on the roadway can be concluded. The reference wavelength, which is not noticeably absorbed by ice or water, e.g., 1300 nm, is used as a reference variable for evaluating the degree of absorption of the two other wavelengths. The measured intensity ratios at the wavelengths 1550 nm/1300 nm can then be related to the ratio 1460 nm/1300 nm in a known manner to obtain formation about water and ice on the roadway or a dry roadway.

The various wavelengths can therefore be emitted in parallel, but particularly sequentially offset in time. Only light of one wavelength is therefore emitted and correspondingly detected at one point in time. This allows complex spectral analysis or beam splitting to be omitted.

The sensor 2 also has an analysis unit 50, by which the data detected or ascertained by the first detector 22 and the second detector 32 are processed. The analysis unit 50 can be arranged outside the housing 4 and can be located at another location in the vehicle 60, for example. The analysis unit 50 can be connected to the first detector 22 and the second detector 32 via a cable or a wireless connection. The analysis unit can also comprise a controller for the light source unit 21 or can be connected to a controller. The analysis unit 50 and/or the controller can also be arranged on or in the housing 4 or integrated therein, however, as shown with reference to FIG. 2.

Using the described sensor 2, with a compact and cost-effective structure, both spectral reflection and also specular and diffuse reflection can be measured in a short chronological sequence and the roadway type and state can be concluded based thereon. As a result, more precise information about the type and the actual state of the roadway 1 or the roadway surface 1a under the vehicle 60 can be obtained. Only the one sensor 2 is required for the measurement.

If only spectral reflection is to be measured, since the measuring precision is sufficient for this purpose, for example, the second detector section 30 can optionally be omitted.

Furthermore, the device 9 has a stoppage ascertainment unit 7. The stoppage ascertainment unit 7 can be connected to the surface sensor 2 or the analysis unit 50 of the surface sensor 2, as shown with reference to FIG. 2, or integrated in the surface sensor 2, as shown in FIG. 3.

To ascertain whether the vehicle 60 is stationary or is to be brought to a stop, the stoppage ascertainment unit 7 can be connected to velocity sensors 74, which are arranged on the wheels of the vehicle to measure the travel velocity, for example, and can obtain information about the current vehicle velocity or the change of the vehicle velocity. The stoppage ascertainment unit 7 can additionally or alternatively also be connected to a transit stop brake 76, as are provided in buses in public transit in particular, for example. These transit stop brakes 76 only allow the opening of the doors 61, 62 when the vehicle 60 is safely stopped and the transit stop brake 76 is engaged. The transit stop brake 76 per se and its mode of operation are well known to a person skilled in the art. Unintentional opening of the doors 61, 62 can therefore be prevented. Information that the transit stop brake 76 has been activated can be used as stoppage information by the stoppage ascertainment unit 7.

An output unit 8 is connected to the stoppage ascertainment unit 7 and the analysis unit 50 of the surface sensor 2. The output unit 8 queries information from the stoppage ascertainment unit 7 and the analysis unit 50 at predetermined intervals and/or receives a corresponding signal from the stoppage ascertainment unit 7 and the analysis unit 50 when it has been recognized that the vehicle 60 is stationary or is to be brought brought to a stop or when a hazardous underlying surface 1 has been ascertained. The output unit 8 can comprise the display unit 85 and/or the projector 82 for outputting a warning signal, as described with reference to FIG. 1, or can relay a corresponding signal to another unit. The warning signal can also comprise a warning tone. The output unit 8 can also output a control signal in order not to release a door lock and/or a coupling unit for a trailer or only to release it after separate confirmation, when the underlying surface has been recognized to be hazardous.

FIG. 3 shows a further example of a device 9. The features shown and described with reference to FIG. 3 can be combined or exchanged with the features shown and described with reference to FIG. 2, depending on the application.

The sensor shown in FIG. 3 corresponds to the sensor described with reference to FIG. 2, with the difference that no light source polarizer is provided. The emitted light beam 110 is not polarized in this case. In order to nonetheless be able to filter out specularly reflected light, a second polarization filter 34 is arranged in the beam path in front of the second detector 32. The polarization direction of the second polarization filter 34 is substantially perpendicular to the polarization direction of the first polarization filter 24. All remaining elements of the sensor 2 can correspond to those of the sensor described with reference to FIG. 1.

In the example shown in FIG. 3, neither a water film 71 nor an ice layer 72 is located on the roadway surface 1a.

In the example shown in FIG. 3, the first axis 20b, which can correspond to the optical axis of the first converging optic 26 and/or of the entire first detector section 20, is aligned at an angle α to the emitter axis 10a, wherein the angle α is at most approximately 10°. Correspondingly, the second axis 30b, which can correspond to the optical axis of the second converging optic 36 and/or of the entire second detector section 30, is aligned at an angle β to the emitter axis 10a, wherein the angle β is also at most approximately 10°. The point of intersection 40 of the emitter axis 10a with the first axis 20b and/or the second axis 30b can lie on the roadway surface 1a or can lie at a distance of up to 50 cm from the roadway surface 1a.

Furthermore, the possibility exists of providing both a light source polarizer or light source polarization filter 14 on the light source unit 12, as described with reference to FIG. 1, and also a second polarizer or second polarization filter 34 on the second detector 32. The polarization directions of the light source polarization filter 14 and the second polarization filter 34 are then aligned parallel to one another. The polarization directions of the light source polarization filter 14 and the second polarization filter 34 of the second detector 32 are arranged substantially perpendicular to the polarization direction of the first polarizer or first polarization filter 24, however.

Furthermore, the analysis unit 50 is shown arranged inside the housing 4 of the sensor 2 or integrated in the housing 2 in FIG. 3. The analysis unit can also be provided outside the sensor 2, as shown in FIG. 1.

The sensor 2 and particularly the emitter optic 16 and the first converging optic 26 or, optionally, also the second converging optic 36 can be designed for the purpose of being arranged at a specific height or a specific height range over the roadway surface 1a. For example, the sensor 2 can be designed for the purpose of being arranged at a height h or a distance of approximately 10 cm to approximately 1 m from the roadway surface 1a, wherein the distance can be adapted to a respective intended purpose. The height h can be in the range of approximately 10 cm to 40 cm for the use of the sensor 2 in a passenger automobile. In the event of use of the sensor 2 in a utility vehicle, an omnibus, or an off-road vehicle, the height can be approximately 30 cm to approximately 100 cm, in particular in a range from 50 cm to 80 cm.

In the example shown in FIG. 3, the stoppage ascertainment unit 7 and the output unit 8 are additionally arranged in the housing 4 of the sensor 2 and connected to the analysis or control unit 50 or integrated therein.

The stoppage ascertainment unit 7 can be connected to a velocity sensor 74 and/or a transit stop brake 76 as described above.

In one example, the sensor 2 can also be used as a movement sensor. In this case, the analysis unit 50 or the stoppage unit 7 can be designed for the purpose of detecting the light intensity of the diffusely reflected light detected in the first detector 22 and/or the reflected light detected in the second detector 32 over time and determining whether the light intensity changes more than within a predefined variance or fluctuation range. If the vehicle is stationary, nothing changes in the reflected light, i.e., in the light incident on the first detector unit 20, and the intensity variations remain within a variance determined by the sensor structure. As long as the intensity variation remains within this variance, the vehicle is not moving. However, if the vehicle moves, even slowly, the detected light intensity changes more strongly due to the differing reflection of the emitted light on the roadway surface 1a. Therefore, a threshold value or a variance can be provided, which allows it to differentiate between a vehicle movement and the absolute vehicle stoppage. It is therefore possible to detect vehicle movements of less than 3 km/h or 1 m/s. It is also possible, for example, to detect vehicle velocities in the range of approximately 0.1 m/s or less. To detect the vehicle movement, the sensor 2 has the stoppage ascertainment unit 7 or can have a separate control unit. This control unit can be comprised in an analysis unit 50 for the sensor 2 or in the stoppage ascertainment unit 7 or can be additionally attached to the sensor, so that a commercially-available surface sensor 2, 102 becomes a movement sensor.

The device 9 of the present description is also designed for retrofitting on existing vehicle 60.

Figure 4:
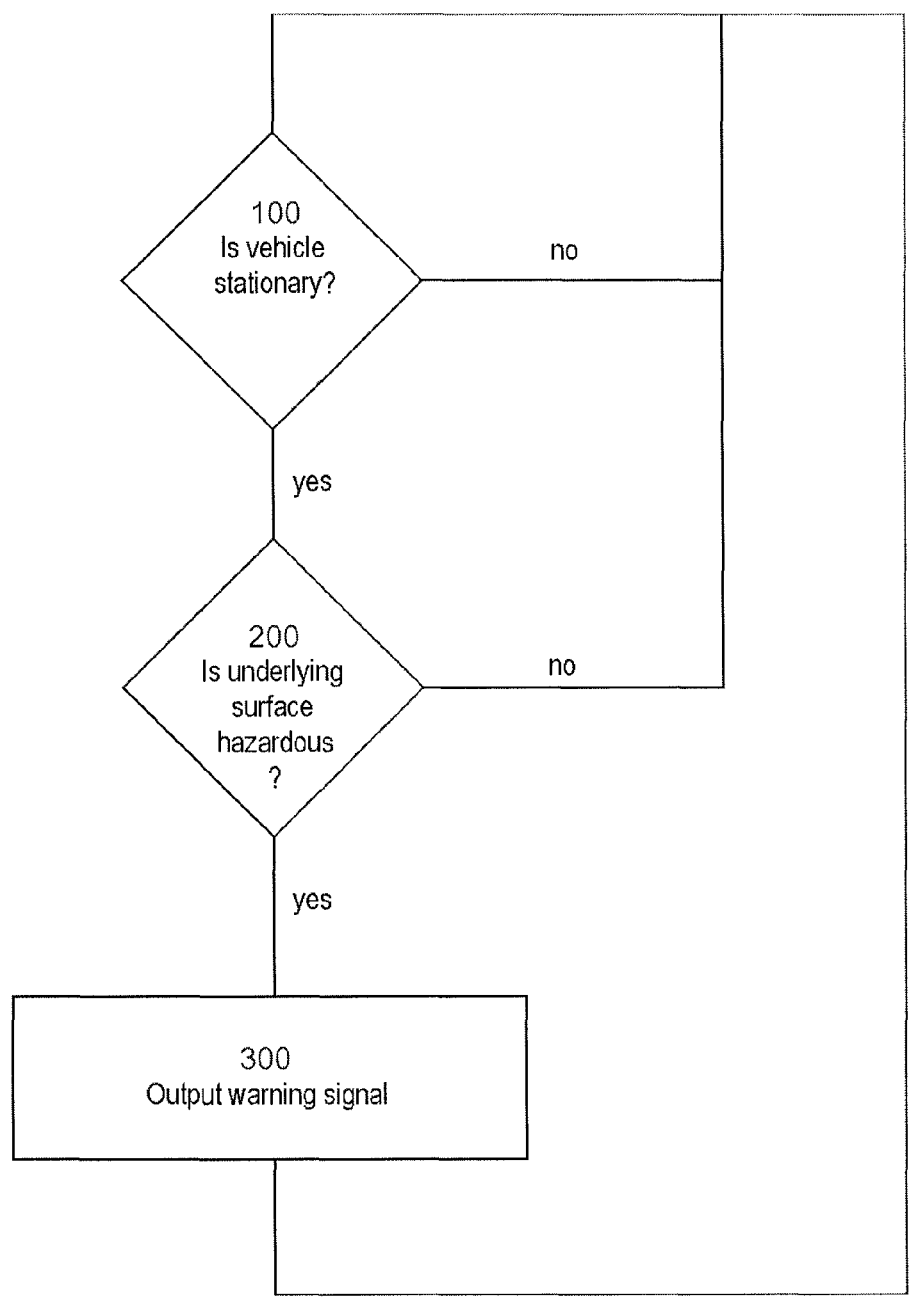
FIG. 4 schematically illustrates a method for outputting a signal when there is a hazardous surface underlying a vehicle according to an embodiment of the present invention.

FIG. 4 shows an example of a method according to the invention. The method can be executed in the output unit 8, for example. In step 100, the stoppage ascertainment unit 7 is queried as to whether the vehicle 60 is stationary or is to be brought to a stop. This step can be repeated at predetermined intervals, or as a function of a brake actuation or the actuation of a door opener, for example.

In step 200, the surface sensor 2 is queried as to whether a hazardous underlying surface 1, or a hazardous roadway condition, has been recognized. Step 200 can also be performed periodically at a predetermined interval and can be performed independently of the result of step 100. However, it can also be provided that the query as to whether a hazardous underlying surface 1 or a hazardous roadway condition has been recognized according to step 200 is only executed when it has been ascertained in step 100 that the vehicle 60 is stationary or is to be brought to a stop.

If it was ascertained in step 100 that the vehicle 60 is stationary or is to be brought to a stop and in step 200 that a hazardous underlying surface 1 or a hazardous roadway condition exists, a signal, for example, a warning signal or a control signal for a further unit, such as a display unit 85 or a projector 82, is output in step 300.

Alternatively, it can also be provided that step 200 of establishing whether the underlying surface is hazardous is performed before or parallel to step 100 of establishing whether the vehicle is stationary or is to be brought to a stop.

The preceding description was provided with regard to the examples shown in the figures. However, a person skilled in the art will readily modify or combine the specified examples and supplement the with further warning signals or control signals, for example. A person skilled in the art will also find further possible applications of the device according to the invention and the method according to the invention, for example, attachment to other points of a vehicle.

A person skilled in the art will also consider wavelengths other than those specified to adapt the measurement results to different requirements. The specified wavelengths are not restricted to precisely these values, but rather can comprise a wavelength range that contains the specified discrete wavelengths.

It will thus be seen that the objects set forth above, among those made apparent from the preceding description, are efficiently attained, and since certain changes may be made without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described and all statements of the scope of the invention that, as a matter of language, might be said to fall therebetween.

What is claimed is:

1. A device for outputting a signal when there is a hazardous underlying surface under a vehicle, the device comprising:
    an optical surface sensor configured to determine at least one parameter of the underlying surface;
    a stoppage ascertainment unit configured to determine whether the vehicle is stationary or is to be brought to a stop; and
    an output unit configured to output a signal:
        (i) when the underlying surface has been determined to be hazardous on the basis of the at least one parameter; and
        (ii) whether the vehicle is stationary or is to be brought to a stop.

2. The device as claimed in claim 1, wherein the output unit comprises a display unit arranged one of on or in proximity to a vehicle door.

3. The device as claimed in claim 1, wherein the optical surface sensor is arranged one of on or in proximity to a vehicle door.

4. The device as claimed in claim 1, wherein the hazardous underlying surface is at least one of a soft and slippery underlying surface.

5. The device as claimed in claim 1, wherein the optical surface sensor comprises:
    a light source unit configured to emit light of at least one wavelength onto the underlying surface, and
    at least one first detector configured to detect light reflected from the underlying surface.

6. The device as claimed in claim 5, wherein the light source unit and the at least one first detector are arranged in a housing.

7. The device as claimed in claim 1, wherein the stoppage ascertainment unit is connected to the optical surface sensor and is configured to receive data from the optical surface sensor.

8. The device as claimed in claim 1, wherein the device is configured to attach to the vehicle.

9. A method for outputting a signal when there is a hazardous underlying surface under a vehicle, the method comprising:
    emitting at least one light beam onto the underlying surface;
    detecting light reflected on the underlying surface;
    ascertaining on the basis of the detected reflected light whether the underlying surface is hazardous;
    ascertaining whether the vehicle is stationary or is to be brought to a stop; and
    outputting a signal:
        (i) when the underlying surface has been ascertained to be hazardous; and
        (ii) the vehicle is stationary or is to be brought to a stop.

10. The method as claimed in claim 9, wherein ascertaining whether the vehicle is stationary or is to be brought to a stop comprises detecting at least one of actuation of a parking brake, actuation of a transit stop brake, shutdown of the engine, disengagement of a safety belt, and opening of a vehicle door.

11. The method as claimed in claim 9, wherein ascertaining whether the underlying surface is hazardous includes detecting at least one of water, snow, ice, grass, and a soft underlying surface.

12. The method as claimed in claim 9, wherein emitting at least one light beam onto the underlying surface is effected in a region of a vehicle door.

13. The method as claimed in claim 9, wherein emitting at least one light beam onto the underlying surface includes light of at least one wavelength in the infrared range.

14. The method as claimed in claim 9, wherein ascertaining whether the vehicle is stationary or is to be brought to a stop is effected on the basis of the detected reflected light.

15. The device as claimed in claim 4, wherein the hazardous underlying surface is covered by at least one of water, snow, ice, and grass.

16. The method as claimed in claim 13, wherein the light includes three wavelengths in the infrared range.

17. The method as claimed in claim 16, comprising:
    comparing measured intensity ratios of the three wavelengths to determine whether the underlying surface is hazardous.

18. The method as claimed in claim 16, comprising:
    emitting the three wavelengths in parallel and sequentially offset in time.

19. The device as claimed in claim 5, further comprising:
    a light source polarizer that polarizes light emitted by the light source unit; and an emitter optic that at least one of focuses and aligns light emitted from the light source unit on a region of the underlying surface.

20. The device as claimed in claim 19, further comprising:
a first converging optic that directs the light emitted by the light source to a first detector of the at least one first detector; and
a first polarization filter arranged substantially perpendicularly with respect to the light source polarizer that prevents specularly reflected light from reaching the first detector such that substantially only diffusely reflected light reaches the first detector.

21. The device as claimed in claim 20, further comprising:
a second converging optic that directs the light emitted by the light source to a second detector of the at least one first detector.

22. The device as claimed in claim 21, further comprising:
a second polarization filter arranged substantially parallel with respect to the light source polarizer that such that substantially only specularly reflected light reaches the second detector.

23. The device as claimed in claim 1, wherein the output unit comprises an optical projector that projects a warning signal in a region of the underlying surface in proximity to a vehicle door.

* * * * *